United States Patent
Torigoe

(10) Patent No.: US 10,117,630 B2
(45) Date of Patent: Nov. 6, 2018

(54) FLUOROSCOPY APPARATUS AND FLUOROSCOPY METHOD

(71) Applicant: SHIMADZU CORPORATION, Kyoto (JP)

(72) Inventor: Yui Torigoe, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 200 days.

(21) Appl. No.: 14/906,453

(22) PCT Filed: Jul. 25, 2013

(86) PCT No.: PCT/JP2013/070194
§ 371 (c)(1),
(2) Date: Jan. 20, 2016

(87) PCT Pub. No.: WO2015/011816
PCT Pub. Date: Jan. 29, 2015

(65) Prior Publication Data
US 2016/0157955 A1    Jun. 9, 2016

(51) Int. Cl.
*A61B 6/00* (2006.01)
*A61B 6/12* (2006.01)
(Continued)

(52) U.S. Cl.
CPC .............. *A61B 6/487* (2013.01); *A61B 6/12* (2013.01); *A61B 6/4014* (2013.01);
(Continued)

(58) Field of Classification Search
CPC ...... A61B 2090/376; A61B 2090/3966; A61B 6/12; A61B 6/4014; A61B 6/4266;
(Continued)

(56) References Cited

U.S. PATENT DOCUMENTS 6,307,914 B1    10/2001    Kunieda et al.
2005/0054916 A1    3/2005    Mostafavi
(Continued)

FOREIGN PATENT DOCUMENTS

JP          3053389          6/2000
JP    2000167072 A *    6/2000    ............... A61B 6/12
(Continued)

OTHER PUBLICATIONS

PCT/JP2013/070194, International Search Report, dated Aug. 27, 2013, 2 pages—English, 3 pages—Japanese.
(Continued)

*Primary Examiner* — Chih-Cheng Kao
(74) *Attorney, Agent, or Firm* — Andrew F. Young, Esq.; Lackenbach Siegel, LLP

(57) ABSTRACT

An image including the marker M is continuously collected every constant time from the images and template matching is performed by utilizing the first template image stored in advance in the template image memory element relative to the image including the marker M. And the image including the marker M after pattern matching specified by the template matching element is clipped as a template image and is stored in the template image memory. Then, the image including the marker M is acquired from the next images continuously collected every constant time. Thereafter, the template matching is performed by utilizing the second template image stored just therebefore in the template image memory element relative to the image including the marker M. Once the second template matching is completed, the image including the marker M is clipped as the next second template image since the pattern matching is identified by the template matching element, and is stored. For the next template matching, the second template image newly stored is utilized.

10 Claims, 11 Drawing Sheets

(51) Int. Cl.
*A61B 90/00* (2016.01)
*G06T 7/246* (2017.01)
*A61N 5/10* (2006.01)

(52) U.S. Cl.
CPC .......... *A61B 6/4266* (2013.01); *A61B 6/5235* (2013.01); *A61B 90/39* (2016.02); *A61N 5/1049* (2013.01); *G06T 7/248* (2017.01); *A61B 6/4464* (2013.01); *A61B 6/54* (2013.01); *A61B 2090/376* (2016.02); *A61B 2090/3966* (2016.02); *A61N 2005/1061* (2013.01); *G06T 2207/10121* (2013.01); *G06T 2207/30061* (2013.01); *G06T 2207/30204* (2013.01)

(58) Field of Classification Search
CPC .. A61B 6/487; A61B 6/54; A61N 2005/1061; A61N 5/1049; G06T 2207/10121; G06T 2207/30061; G06T 2207/30204; G06T 7/248
See application file for complete search history.

(56) References Cited

U.S. PATENT DOCUMENTS

| | | |
|---|---|---|
| 2006/0074292 A1 | 4/2006 | Thomson et al. |
| 2008/0317312 A1 | 12/2008 | Carl et al. |
| 2011/0087061 A1 | 4/2011 | Handa et al. |

FOREIGN PATENT DOCUMENTS

| | | |
|---|---|---|
| JP | 2004-533889 | 11/2004 |
| JP | 2007-503926 | 3/2007 |
| JP | 2008-514352 | 5/2008 |
| JP | 2009-540972 | 11/2009 |
| JP | 2011-234932 | 11/2011 |
| JP | 2012-170767 | 9/2012 |
| WO | WO 2010/103623 | 12/2010 |
| WO | WO 2011/117789 | 9/2011 |
| WO | WO 2011/163414 | 12/2011 |

OTHER PUBLICATIONS

JP Office Action in JP2015-528072 (now allowed), dated Aug. 23, 2016 (Japanese (4 pages) and English translation (5 pages)).

* cited by examiner

FLUOROSCOPY APPARATUS AND FLUOROSCOPY METHOD

CROSS REFERENCE TO RELATED INVENTIONS

This application claims priority from and is a § 371 of Ser. No.: PCT/JP2013/070194 filed Jul. 25, 2013, the entire contents of which are incorporated herein by reference.

FIGURE SELECTED FOR PUBLICATION

FIG. 8

BACKGROUND OF THE INVENTION

Field of the Invention

The present invention relates to an X-ray fluoroscopic device and a method of X-ray fluoroscopy using the same in order to specify the position of the marker or the specific area by continuously detecting and collecting images including the marker indwelled inside the subject's body or the specific area of the subject with an X-ray detector.

Description of the Related Art

The radiation relative to a radiation therapy, in which the radiation including an X-ray and an electron beam and so forth is irradiated to the affected area including a tumor and so forth, must be accurately irradiated to the affected area. Nevertheless, in some cases, not only the subject unintentionally moves the body thereof, but also the affected area per se moves. For example, a tumor near the lung largely moves depending on breathing. Accordingly, a radiation therapeutic device comprising the system, in which the X-ray fluoroscopic device detects the position of a metal marker in-place near the tumor and then the therapeutic radiation to be irradiated is controlled thereby, is disclosed (refer to Patent Document 1.)

According to such radiation therapeutic device, the fluoroscopic image is collected by detecting the marker indwelled in the body using the first X-ray fluoroscopic mechanism comprising a first X-ray tube and a first X-ray detector and the second X-ray fluoroscopic device mechanism comprising a second X-ray tube and a second X-ray detector and then a three-dimensional position information is obtained by utilizing the two-dimensional fluoroscopic image based on the first X-ray fluoroscopic mechanism and the two-dimensional fluoroscopic image based on the second X-ray fluoroscopic mechanism. And, the real-time three-dimensional position information of the marker is calculated by performing the continuous X-ray fluoroscopy so that the marker of the region along with move can be detected with a high degree of accuracy, and radiation of the therapeutic radiation is controlled based on the position information of the marker so that the irradiation of the radiation corresponding to the move of the tumor can be performed with a high degree of accuracy, accordingly. When the position information of the marker is obtained, the template matching utilizing the template image is performed.

FIG. 11 is an explanatory drawing illustrating the conventional template matching operation.

First of all, a template corresponding to the marker M is prepared for performing the template matching. In such case, the image 70 of the subject including the marker M is imaged. And, the template image 71 is obtained by extracting the marker M region from the image 70. On performing fluoroscopy, the template matching is conducted using the template image 71 relative to the region 73 where the marker M exists relative to the image 72 of the subject, which is collected at a constant framing rate, so that the position of the marker M can be identified.

The marker M used in such radiation therapeutic device has conventionally a sphere-like shape therefor. Specifically, when the template matching is performed relative to the image 72 of the subject, which is collected at a constant framing rate, utilizing the template image 71, if such spherical marker M is used, the imaging of the marker M from any directions provides a circle image so that the template matching can be performed effectively with just preparing only the marker having a circular shape as a template image.

On the other hand, it is problematic that the spherical marker M is hardly indwelled inside the body of the subject. Specifically, when a spherical marker M is employed, it can be slippery against and hardly hooked to the viscera due to the shape per se thereof so that even once it is indwelled inside the body, it will likely drop out from the indwelled region in-place. Accordingly, a number of markers M are indwelled inside the body in advance while predicting that such drop-out will take place and then the marker M that has not dropped out is being utilized, in some cases. Nevertheless, in such case, it is problematic that a wasteful expense may be incurred in order to indwell a number of markers M and the longer surgery time for indwelling may burden the subject.

Consequently, a coil-type marker and non-spherical marker recently have been proposed (refer to Patent Document 2 and Patent Document 3.) According to these devices of Patent Document 2 and Patent Document 3, a template matching is performed by utilizing the image including the marker.

PRIOR ART

Patent Document

Patent Document 1: JP Patent 3053389 B1
Patent Document 1 JP Patent Published 2011-234932 A
Patent Document 3: JP Patent Published 2012-170767 A

Aspects and Summary of the Invention

In response, it is now recognized that there is a need for an improved x-ray fluoroscopic device and method of x-ray fluoroscopy using the same.

Problems to be Solved by the Invention

As disclosed in Patent Document 2, for example, when the coil-type marker is employed, the marker can be indwelled stably inside the body of the subject. However, when the non-spherical marker such as the coil-type marker and so forth is employed, the recognizable shape of the marker varies differently depending on the imaging angle so that even if the template is generated by utilizing the image imaging the marker, it can be problematic because such template cannot be utilized for the template matching.

The same kind of problem may also take place even when the marker is replaced with the specific region such as the patient's tumor area instead of the marker.

In addition, differently from the above described problem, even when either spherical marker or non-spherical marker is employed, if the template image utilizing the image including the marker is generated, the bone that is a structure inside the body of the subject is imaged together with the marker, and therefore the problem, in which the template matching cannot be accurately performed, takes place. Specifically, when the bone is imaged with the marker, the contrast and so forth of the marker varies differently every continuously collected image so that the matching may not be operative even if the template matching is conducted using the single marker.

The purpose of the present invention is to provide the solution for the above problem and is to provide the X-ray fluoroscopic device and X-ray fluoroscopic method that can suitably recognize the marker or the specific region by the template matching and can accurately identify the position of the marker or the specific region, when the non-spherical marker is employed, when the specific region of the patient is employed instead of the marker, and even when the marker is imaged together with the body structure such as a bone and so forth.

Means for Solving the Problem

According to the first invention, an X-ray fluoroscopic device comprises an X-ray tube, and an X-ray detector that detects the X-ray that is irradiated from the X-ray tube and passes through the subject, and specifies the position of the marker or the specific region by collecting images including the marker indwelled inside the subject's body or the specific region of the subject; and further comprises a template image memory element that stores the image including the marker or the specific region as a template image, a template matching element that specifies the position of the marker or the specific region relative to the continuously collected images by performing template matching utilizing the template image stored in the template image memory element relative to the continuously collected images, and a template clipping element that clips the image including the marker or the specific region specified by the template matching element as a template image and that lets the template image memory element stores; and the template matching element performs the template matching by utilizing the template image, which is clipped from the image collected prior to collection of the image continuously collected and stored in the template image memory element, relative to the continuously collected images.

According to the second invention, the template matching element performs the template matching by utilizing the template image, which is clipped from the image collected prior to collection of the image relative to the continuously collected images.

According to the third invention, a plurality of template images clipped from the continuously collected images are stored in the template image memory element, and the template matching element performs the template matching by utilizing the plurality of the template images, which are stored in the template image memory element relative to the continuously collected images.

According to the fourth invention, the template matching element performs the template matching by preferentially-utilizing the template image, which is clipped from the images collected at the time closer to the collection time of the image thereof among a plurality of template images stored in the template image memory element relative to the continuously collected images.

According to the fifth invention, an X-ray fluoroscopic method for specifying the position of the marker or the specific region by a step of detecting the X-ray that is irradiated from an X-ray tube and passes through the subject by the X-ray detector and a step of specifying the position of a marker or a specific region by collecting images including the marker indwelled inside the subject's body or the specific region of the subject comprises; a template image storing step of storing the template image including the marker or the specific region as the first template image; a first template matching step of specifying the position of the marker or the specific region relative to the continuously collected images by performing template matching utilizing the first template image relative to the continuously collected images; a template clipping step clipping the images including the marker or the specific region specified by the first template matching step, and storing as a second template image; and a second template matching step of specifying the position of the marker or the specific region relative to the continuously collected images by performing template matching utilizing the second template image relative to the continuously collected images.

According to the sixth invention, the template clipping step and the second template matching step are performed multiple times relative to the continuously collected images; wherein in the second template matching step, the template matching is performed by utilizing the second template image clipped from the image collected just prior to the collection of the image relative to the continuously collected images.

According to the seventh invention, the template clipping step and the second template matching step are performed multiple times relative to the continuously collected images; wherein in the second template matching step, the template matching is performed by utilizing the plurality of the second template images relative to the continuously collected images.

According to the eighth invention, the template matching is performed by preferentially-utilizing the second template image clipped from the images collected at the time closer to the collection time of the image among a plurality of second template images relative to the continuously collected images.

Effect of the Invention

According to the first and fifth inventions, even when the non-spherical marker is employed, when the specific region of the patient is employed, or when the marker is imaged together with the body structure, the marker or the specific region can be suitably recognized by the template matching so that the position of the marker or the specific region can be accurately identified, According to the second and sixth inventions, the template image clipped from images collected just prior to the collection, which are considered similar to the collected image, is being utilized so that the template matching can be accurately and expeditiously performed.

According to the third and seventh inventions, a plurality of the template images are utilized so that possibilities of an occurrence of miss matching on the template matching can be lowered.

According to the fourth and eighth inventions, the template image clipped from images collected in closer timing is being preferentially-utilized so that the template matching can be expeditiously and efficiently performed.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
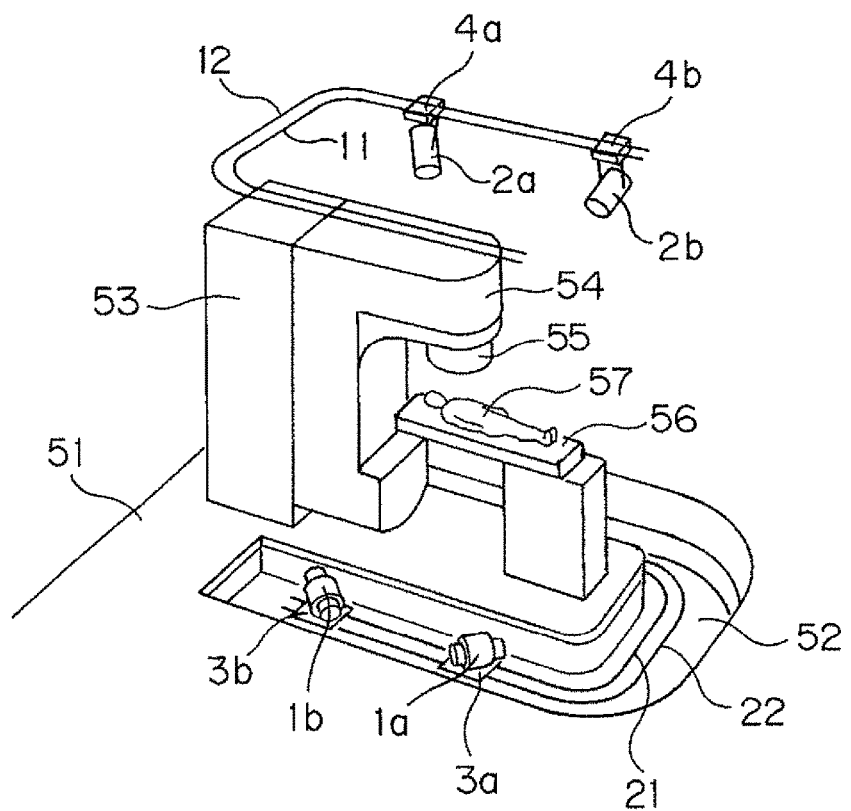
FIG. 1 is a perspective view of the radiation therapeutic device applying the X-ray fluoroscopic device of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 2:
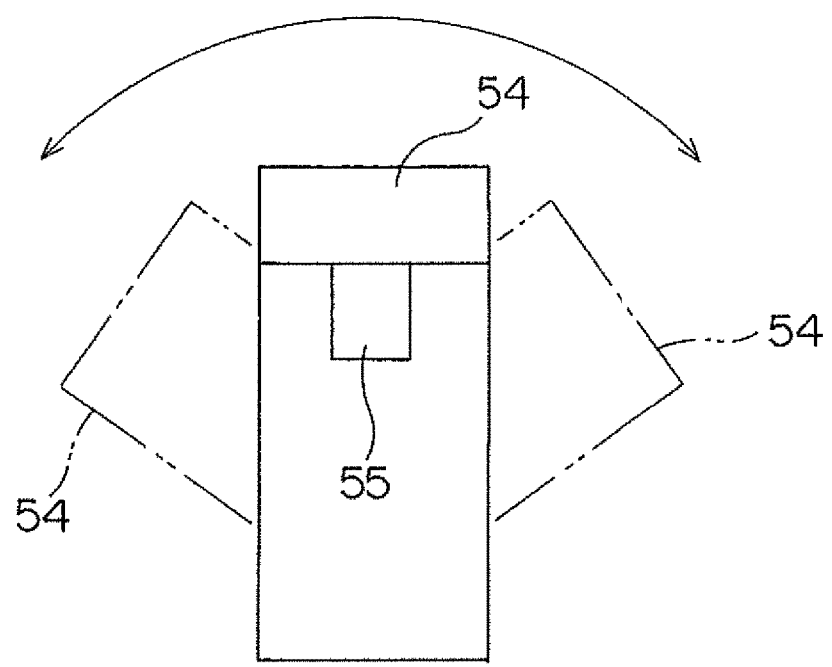
FIG. 2 is an explanatory drawing of the oscillating operation of the head 55 and the head support 54 relative to the radiation therapeutic device.

The inventor sets forth Embodiments of the present invention based on the following FIGs. FIG. 1 is a perspective view of the radiation therapeutic device applying the X-ray fluoroscopic device of the present invention. FIG. 2 is an explanatory drawing of the oscillating operation of the head 55 and the head support 54 relative to the radiation therapeutic device.

The present radiation therapeutic device is to provide a therapeutic treatment by radiation of an X-ray or an electron beam to the affected area of the subject 57 lying on the imaging table 56 and comprises a gantry 53 installed on the floor 51 of the treatment room, a head support element 54 that oscillates around the axis facing the horizontal direction relative to the gantry 53 and a head 55 supported by the head support element 54 in order to irradiate the radiation to the subject 57. The head 55 is capable of irradiating the radiation to the affected area of the subject 57 from a variety of angles due to the oscillating operation of the head support element 54.

On performing a radiation therapy, the radiation must be accurately irradiated to the affected area. For such purpose, a marker is set near the affected area. The marker indwelled inside the body is continuously looked at through the first X-ray fluoroscopic mechanism and the second X-ray fluoroscopic mechanism and the three-dimensional position information as to the marker is calculated from the two-dimensional fluoroscopic images obtained by the first X-ray fluoroscopic mechanism and the second X-ray fluoroscopic mechanism so that the marker can be structurally detected with a high degree of accuracy.

The X-ray fluoroscopic device of the present invention in order to perform such fluoroscopic operation comprises the first X-ray fluoroscopic mechanism consisting of the first X-ray tube 1a and the first X-ray detector 2a and the second X-ray fluoroscopic mechanism consisting of the second X-ray tube 1b and the second X-ray detector 2b, and further comprises the move mechanism that moves the first X-ray tube 1a and the first X-ray detector 2a to the first fluoroscopic position and the second fluoroscopic position, as described later, so as to place opposite each other and also the second X-ray tube 1b and the second X-ray detector 2b to the first fluoroscopic position and the second fluoroscopic position so as to place opposite each other. Further, for example, an image intensifier (I. I.) or a flat panel detector (FPD) is used as the first. X-ray detector 2a and the second X-ray detector 2b.

The first X-ray tube 1a is supported with the first pedestal 3a for the X-ray tube. Further, the second X-ray tube 1b is supported with the second pedestal 3b for the X-ray tube. The first rail 21 for the X-ray tube having approximately U-shape, in which two linear portions are connected with the connection element including a circular portion, and the second rail 22 for the X-ray tube having approximately U-shape as the same as the first rail 21 for the X-ray tube, in which two linear portions are connected with the connection element including a circular portion, are installed on the bottom surface 52 of the concave portion formed on the floor 51 in the imaging room. The first rail 21 for the X-ray tube and the second rail 22 for the X-ray tube are parallel in-place each other. Then, the first pedestal 3a for the X-ray tube and the second pedestal 3b for the X-ray tube move to the first fluoroscopic position and the second fluoroscopic position, as described later, by guiding with the first rail 21 and the second rail 22.

The first X-ray detector 2a is supported with the first pedestal 4a for the X-ray detector. Further, the second X-ray detector 2b is supported with the second pedestal 4b for the X-ray detector. The first rail 11 for the X-ray detector having approximately U-shape, in which two linear portions are connected with the connection element including a circular portion, and the second rail 12 for the X-ray detector having approximately U-shape as the same as the first rail 11 for the X-ray detector, in which two linear portions are connected with the connection element including a circular portion, are suspended from the ceiling of the imaging room. The first rail 11 for the X-ray detector and the second rail 12 for the X-ray detector are parallel in-place each other. Then, the first pedestal 4a for the X-ray detector and the second pedestal 4b for the X-ray detector move to the first fluoroscopic position and the second fluoroscopic position, as described later, by guiding with the first rail 11 and the second rail 12.

Figure 3:
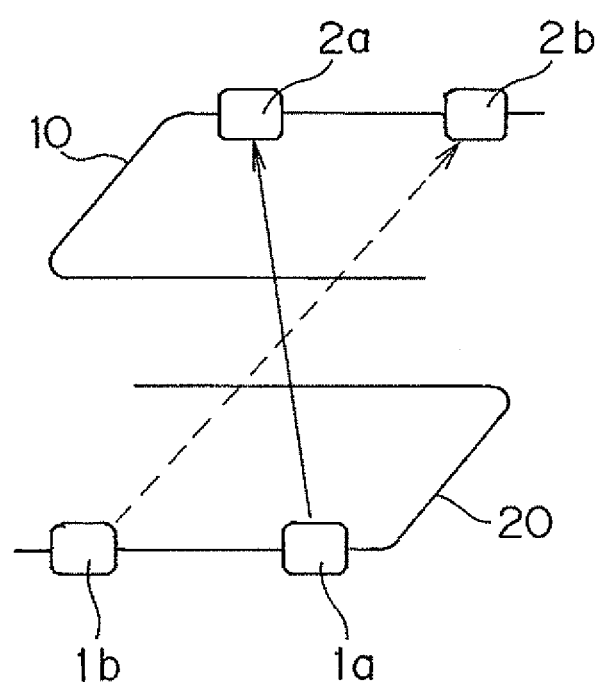
FIG. 3 is an explanatory drawing of the state in-place, in which the first X-ray tube 1a, the second X-ray tube 1b, the first X-ray detector 2a and the second X-ray detector 2b are respectively arranged in the first fluoroscopic position.

FIG. 3, 4, 5 are explanatory drawings of the state in-place, in which each the first X-ray tube 1a, the second X-ray tube 1b, the first X-ray detector 2a and the second X-ray detector 2b are arranged in the first fluoroscopic position and the second fluoroscopic position.

The X-ray fluoroscopic device fluoroscopes the subject 57 structurally from two directions different from each other at three preset positions. FIG. 3 illustrates the state in which the first X-ray tube 1a, the second X-ray tube 1b, the first X-ray detector 2a and the second X-ray detector 2b fluoroscope the subject 57 from two t directions different from each other at the first position.

Figure 4:
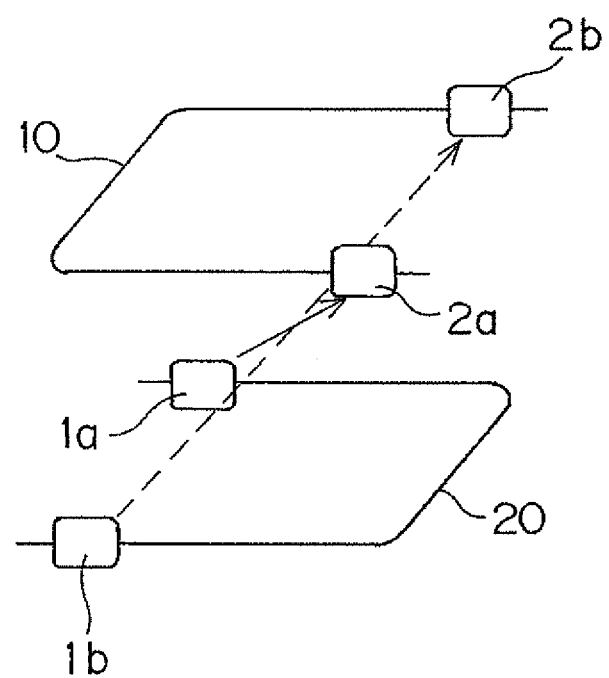
FIG. 4 is an explanatory drawing of the state in-place, in which each the first X-ray tube 1a, the second X-ray tube 1b, the first X-ray detector 2a and the second X-ray detector 2b are arranged in the first fluoroscopic position and the second fluoroscopic position.

FIG. 4 illustrates the state in which the first X-ray tube 1a, the second X-ray tube 1b, the first X-ray detector 2a and the second X-ray detector 2b fluoroscope the subject 57 from two directions different from each other at the second position.

Figure 5:
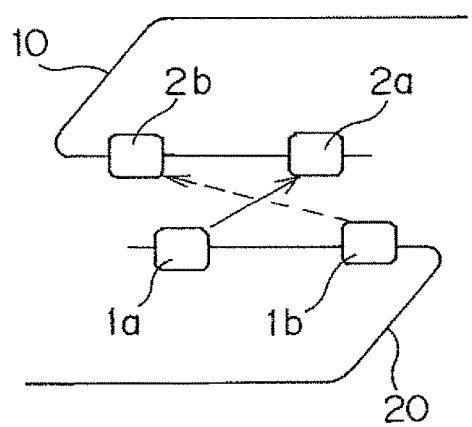
FIG. 5 is an explanatory drawing of the state in-place, in which the first X-ray tube 1a, the second X-ray tube 1b, the first X-ray detector 2a and the second X-ray detector 2b are respectively arranged in the second fluoroscopic position.

FIG. 5 illustrates the state in which the first X-ray tube 1a, the second X-ray tube 1b, the first X-ray detector 2a and the second X-ray detector 2b fluoroscope the subject 57 from two directions different from each other at the third position.

Accordingly, the X-ray fluoroscopic device fluoroscopes structurally the subject 57 from two directions different from each other at the three positions so that, referring to FIG. 2, the head 55 can move without concern to perform X-ray fluoroscopy even when the head 55 of the radiation therapeutic device irradiates the subject 57 from a variety of angles. And at such three positions, the first X-ray tube 1a, the second X-ray tube 1b and the first X-ray detector 2a and the second X-ray detector 2b are arranged in-place in either one of the preset first fluoroscopic position or the preset second fluoroscopic position.

Specifically, referring to FIG. 3, in the first position, the first X-ray tube 1a is arranged in-place in the first fluoroscopic position, the second X-ray tube 1b is arranged in-place in the first fluoroscopic position, the first X-ray detector 2a is arranged in-place in the first fluoroscopic position, and the second X-ray detector 2b is arranged in-place in the first fluoroscopic position, respectively. Referring to FIG. 4, in the second position, the first X-ray tube 1a is arranged in-place in the second fluoroscopic position, the second X-ray tube 1b is arranged in-place in the first fluoroscopic position, the first X-ray detector 2a is arranged in-place in the second fluoroscopic position, and the second X-ray detector 2b is arranged in-place in the first fluoroscopic position, respectively. Referring to FIG. 5, in the third position, the first X-ray tube 1a is arranged in-place in the second fluoroscopic position, the second X-ray tube 1b is arranged in-place in the second fluoroscopic position, the first X-ray detector 2a is arranged in-place in the second fluoroscopic position, and the second X-ray detector 2b is arranged in-place in the second fluoroscopic position, respectively.

The first pedestal 3a for the X-ray tube and the second pedestal 3b for the X-ray tube move along the move passage 20 consisting of the first rail 21 and the second rail 22 so that the first X-ray tube 1a and the second X-ray tube 1b can be arranged in-place in the first fluoroscopic position and the second fluoroscopic position, respectively. Further, the first pedestal 4a for the X-ray detector and the second pedestal 4b for the X-ray detector move along the move passage 10 consisting of the first rail 11 and the second rail 12 so that the first X-ray detector 2a and the second X-ray detector 2b can be arranged in-place in the first fluoroscopic position and the second fluoroscopic position, respectively.

Figure 6:
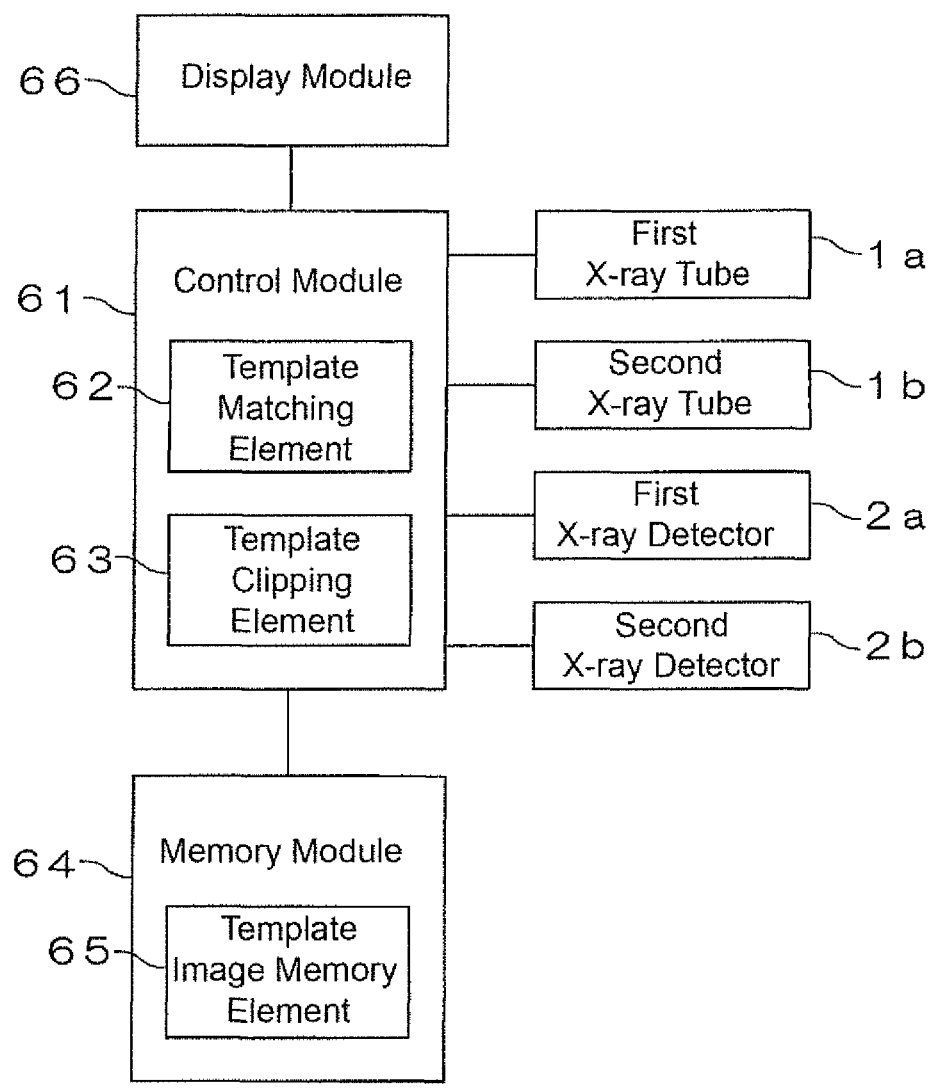
FIG. 6 is a block diagram illustrating the main control system of the X-ray fluoroscopic device of the present invention.

FIG. 6 is a block diagram illustrating the main control system of the X-ray fluoroscopic device of the present invention.

The X-ray fluoroscopic device includes a control module 61 to control the entire device. The control module 61, as described later, comprises the template matching element 62 that specifies in real-time the position of the marker or the specific tumor region relative to the images of the subject 57, continuously collected every constant time, by performing template matching utilizing the first template image and the second template image relative to the images of the subject 57, continuously collected every constant time. Further, the control module 61 comprises a template clipping element 63 that clips the image including the marker or the tumor specified by the template matching element 62 as the second template image and lets it store. In addition, the control module 61 is connected to a display module 66 consisting of the liquid crystal display panel to display the fluoroscopic image and so forth. Further, the control module 61 is also connected to the memory element 64. The memory element 64 includes the template image memory element 65 to store the first template image and the second template image.

The control module 61 is connected, as described above, to the first X-ray tube 1a, the second X-ray tube 1b, the first X-ray detector 2a and the second X-ray detector 2b. Further the control module 61 is connected a driving module, not shown in FIG., as described above, to drive the first pedestal 3a for the X-ray tube, the second pedestal 3b for the X-ray tube, the first pedestal 4a for the X-ray detector, and the second pedestal 4b for the X-ray detector. Further, the control module 61 is also connected to the radiation therapeutic device in FIG. 1.

Figure 7:
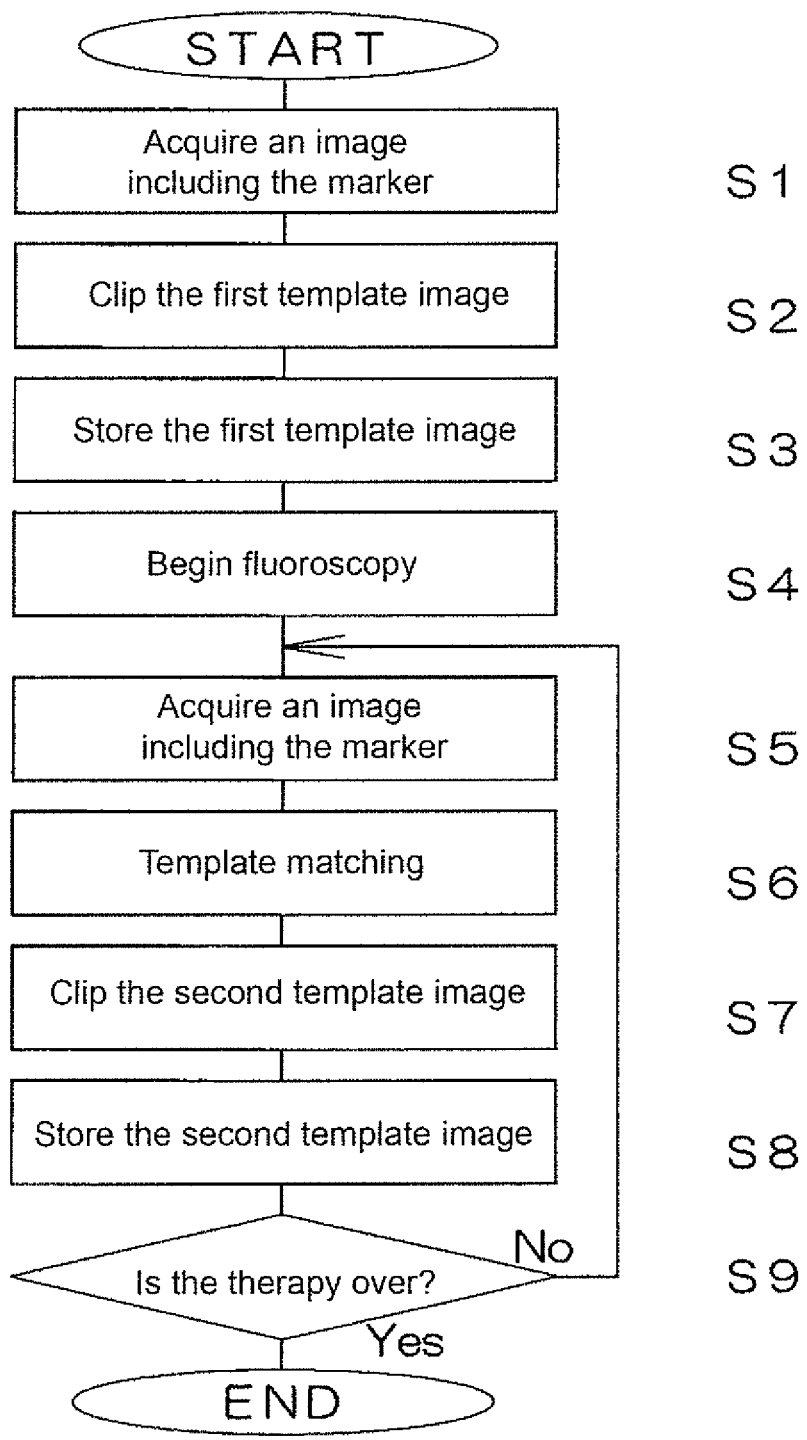
FIG. 7 is a flow-chart illustrating the template matching operation of first Embodiment according to the X-ray fluoroscopic device of the present invention.
Figure 8:
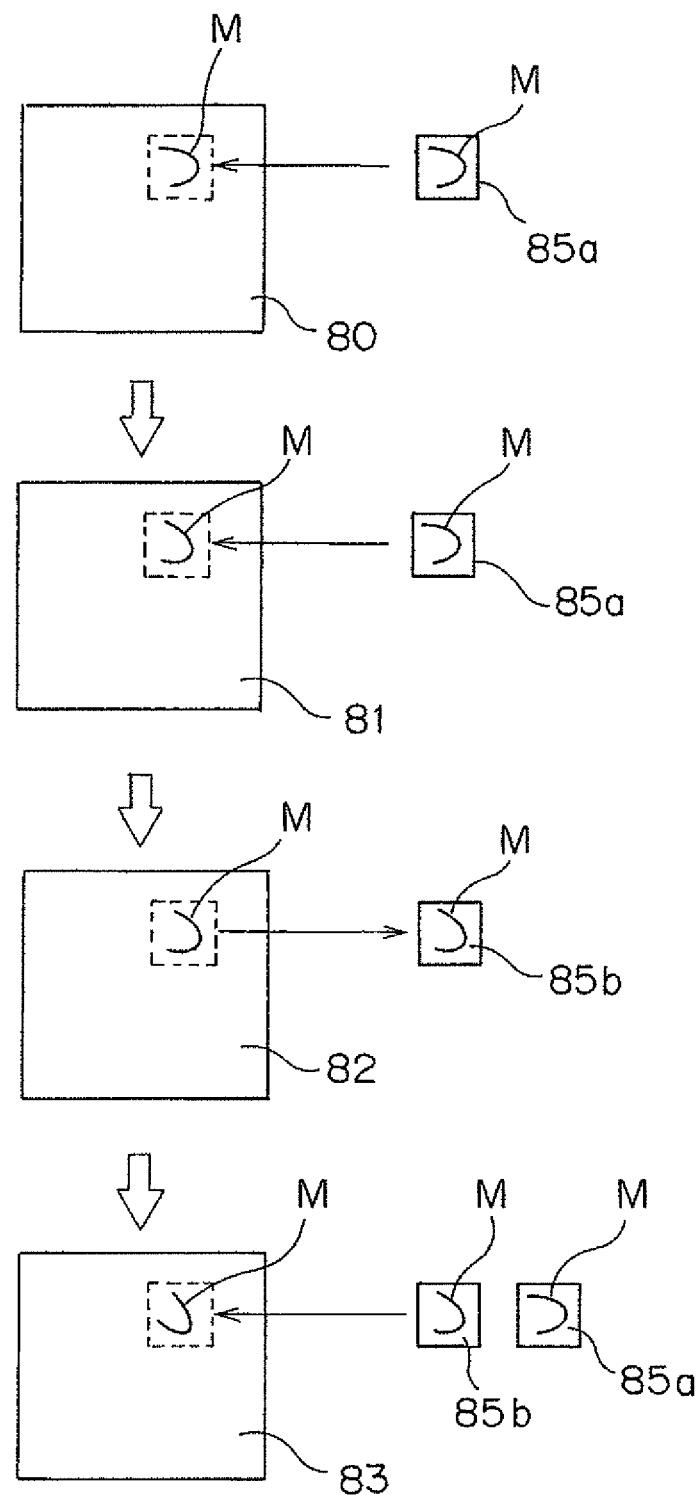
FIG. 8 is an explanatory drawing illustrating the template matching operation of first Embodiment according to the X-ray fluoroscopic device of the present invention.

Next, the inventor sets forth the template matching operation characterizing the present invention. FIG. 7 is a flowchart illustrating the template matching operation of first Embodiment according to the X-ray fluoroscopic device of the present invention. FIG. 8 is an explanatory drawing illustrating the template matching operation of first Embodiment according to the X-ray fluoroscopic device of the present invention. Further, the marker M employed in first Embodiment has a non-spherical shape.

Figure 11:
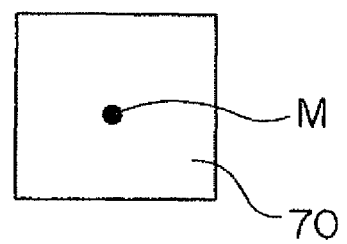
FIG. 11 is an explanatory drawing illustrating the conventional template matching operation.
Figure 11:
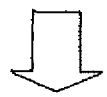
Figure 11:
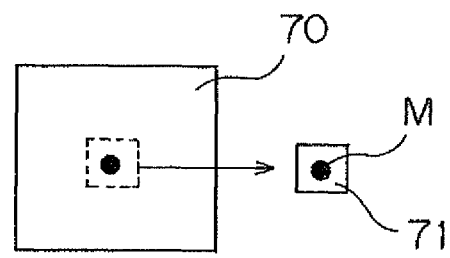
Figure 11:
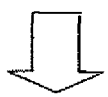
Figure 11:
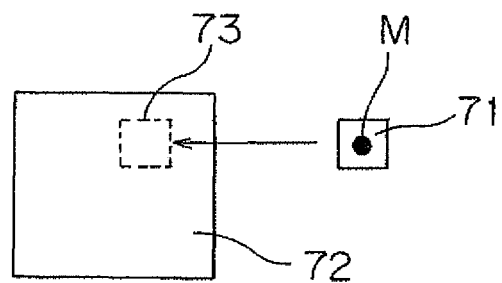

First of all, the template corresponding to the marker M is prepared for performing the template matching. In this case, the images 80 including the marker M are acquired by imaging the subject 57 while the first X-ray tube 1a, the second X-ray tube 1b, the first X-ray detector 2a, the second X-ray detector 2b are arranged in either position illustrated in FIG. 3, FIG. 4. FIG. 5 (Step S1.) And, the first template image 85a is obtained by clipping the marker M region from the image 80 including the marker M (Step S2.) The first template image 85a is stored in the template image memory element 65 illustrated in FIG. 6 (Step S3.) In addition, this step is the same as the conventional template matching illustrated in FIG. 11.

Once the above preparation is completed, the fluoroscopy begins (Step 4) to provide the subject 57 with the therapy. At this time, the X-ray fluoroscopic device of the present invention detects the position of the marker M so that the position of the radiation to be irradiated relative to the affected area of the subject 57 can be adjusted based on the position of the marker M.

At this time, the fluoroscopy is conducted at the framing rate around 30 fps relative to the region including the marker M. Then, referring to FIG. 8, the image including the marker M is acquired from the images 81 continuously collected every constant time (Step S5.) Thereafter, the template matching element 62 illustrated in FIG. 6 performs the template matching by utilizing the first template image 85a stored in advance in the template image memory element 65 relative to the image including the marker M (Step S6.)

In addition, as described above, the images 81 are continuously collected approximately at 30 fps framing rate every constant time. While performing fluoroscopy, if the framing rate is changed, the time interval to continuously collect the images 81 changes.

Once the first template matching is completed, the template clipping element 63 illustrated in FIG. 6 clips the image including the marker M as the second template image 85b since the pattern matching is identified by the template matching element 62 (Step S7) and let it store in the template image memory element 65 (Step S8.)

When the therapeutic treatment continues (Step S9), the step turns back to Step S5 and the image including the marker M is acquired from the next images 82 continuously collected every constant time (Step S5.) Thereafter, the template matching element 62 illustrated in FIG. 6 performs the template matching by utilizing the second template image 85b stored just therebefore in the template image memory element 65 relative to the image including the marker M (Step S6.)

Once the second template matching is completed, the template clipping element 63 illustrated in FIG. 6 clips the image including the marker M as the next second template image since the pattern matching is identified by the template matching element 62 (Step S7) and let it store in the template image memory element 65 (Step S8.) For the next template matching, the second template image newly stored after performing the second template matching is utilized. As well, after the third template matching is completed, the second template image generated and stored after the template matching thereof is employed for the next template matching. Since then, the same operation as these is repeatedly performed.

When the necessary therapeutic operation is completed by repeating these operations (Step S9), the treatment is over.

In addition, when Step S5-Step S8, as described above, are repeatedly performed, a number of the second template images, which are equal to a number of repetitions thereof, are generated and stored in the template image memory element 65. According to Embodiment as described above, the second template image clipped from the images collected just before the collection of the images including the marker among a plurality of the second template images stored in the template image memory element 65 is utilized for the template matching. Because it is deemed that the image of the marker M collected just therebefore is most similar to the image of the marker M collected just thereafter.

At this time, as the other Embodiment, the template matching can be performed by matching, one after the other, a plurality of second template images stored in the template image memory element 65 relative to the images 81, 82, 83 and so forth continuously collected every constant time. In this case, the likelihood in which any one of the plurality of second template images matches to the image of the marker M collected every constant time is high so that the likelihood of an occurrence of miss matching on the template matching can be lowered.

In such wise, it is preferable that when a plurality of second template images stored in the template image memory element 65 are being subject to matching one after the other, the template matching is performed by preferentially-utilizing the second template image, which is clipped from the images collected at the time closer to the collection time of the target image thereof among the plurality of second template images stored in the template image memory element 65. According to adopting such constitution, the template image clipped from images collected in closer timing, on which the likelihood of similarity of the shape of the imaged marker M is high, is being preferentially-utilized so that the template matching can be expeditiously and efficiently performed.

Figure 9:
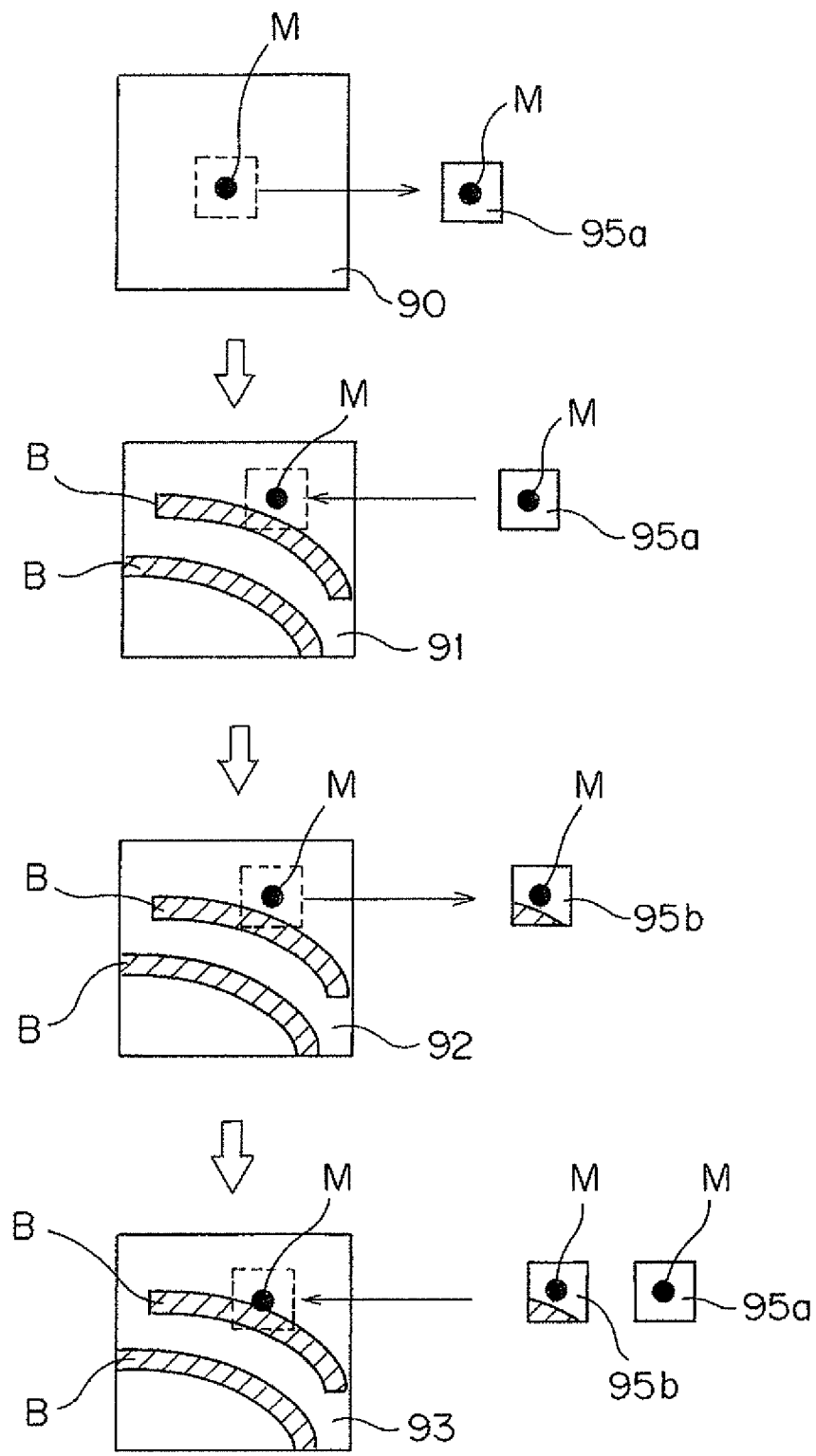
FIG. 9 is an explanatory drawing illustrating the template matching operation of second Embodiment according to the X-ray fluoroscopic device of the present invention.

Next, the inventor sets forth the other Embodiment of the present invention. FIG. 9 is an explanatory drawing illustrating the template matching operation of second Embodiment according to the X-ray fluoroscopic device of the present invention. Further, the marker M employed in this Embodiment has a spherical shape. However, the non-spherical marker M can be used as well as in Embodiment 1.

According to second Embodiment, when the template corresponding to the marker M is prepared, the marker M and the bone region B that is a structure inside the body of the subject 57 are imaged at the same time. In this case, the images 90 including the marker M are acquired by imaging the subject 57 while the first X-ray tube 1a, the second X-ray tube 1b, the first X-ray detector 2a, the second X-ray detector 2b are arranged at either position illustrated in FIG. 3, FIG. 4, FIG. 5 (Step S1.) And, the first template image 95a is obtained by clipping the marker M region from the image 90 including the marker M (Step S2.) The first template image 95a is memorized in the template image memory element 65 illustrated in FIG. 6 (Step S3.)

Once the above preparation is completed, the fluoroscopy begins (Step 4) to provide the subject 57 with the therapy. At this time, the X-ray fluoroscopic device of the present invention detects the position of the marker M so that the position of the radiation to be irradiated relative to the affected area of the subject 57 can be adjusted based on the position of the marker M.

At this time, the fluoroscopy is conducted at the framing rate around 30 fps relative to the region including the marker M. Then, referring to FIG. 9, the image including the marker M and the bone region B is acquired from the images 91 continuously collected every constant time (Step S5.) Thereafter, the template matching element 62 illustrated in FIG. 6 performs the template matching by utilizing the first template image 95a stored in advance in the template image memory element 65 relative to the image including the marker M (Step 6.)

Once the first template matching is completed, the template clipping element 63 illustrated in FIG. 6 clips the image including the marker M and the bone region B as the second template image 95b since the pattern matching is identified by the template matching element 62 (Step S7) and let it store in the template image memory element 65 (Step S8.)

When the therapeutic treatment should continue (Step S9), the step turns back to Step S5 and the image including the marker M and the bone region B is acquired from the next images 92 continuously collected every constant time (Step S5.) Thereafter, the template matching element 62 illustrated in FIG. 6 performs the template matching by utilizing the second template image 95*b* stored just therebefore in the template image memory element 65 relative to the image including the marker M and the bone region B (Step S6.)

Once the second template matching is completed, the template clipping element 63 illustrated in FIG. 6 clips the image including the marker M and the bone region B as the next second template image since the pattern matching is identified by the template matching element 62 (Step S7) and let it store in the template image memory element 65 (Step S8.) For the next template matching, the second template image newly stored is utilized.

When the necessary therapeutic operation is completed by repeating these operations (Step S9), the treatment is over.

In addition, according to second Embodiment, the inventor sets forth the case when the bone region B is imaged with the marker M, but instead of the bone region B, the other structure such as diaphragm inside the body can be imaged with the marker M.

Figure 10:
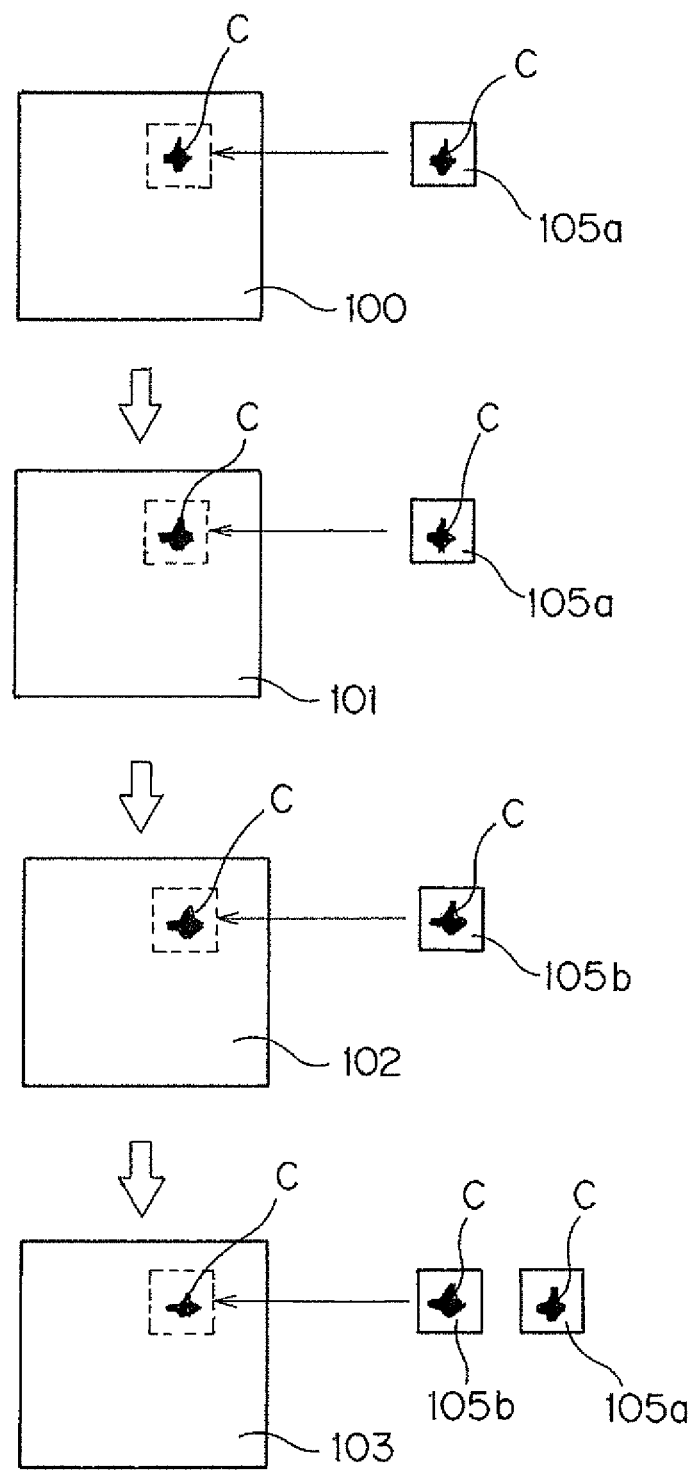
FIG. 10 is an explanatory drawing illustrating the template matching operation of third Embodiment according to the X-ray fluoroscopic device of the present invention.

Next, the inventor sets forth the other Embodiment of the present invention. FIG. 10 is an explanatory drawing illustrating the template matching operation of third Embodiment according to the X-ray fluoroscopic device of the present invention.

According to first Embodiment and second Embodiment as described above, a sphere type or non-sphere type marker M is utilized and the image including the marker M is employed as the template, but in contrast, according to third Embodiment, it is structurally adopted that the image including the specific region of the subject 57 instead of the marker M is employed. Here, for example, the tumor region relative to the subject 57 can be utilized as the specific region.

According to third Embodiment, first of all, the template corresponding to the tumor C, which is the specific region of the subject 57, is prepared for performing the template matching. In this case, the images 100 including the tumor C are acquired by imaging the subject 57 while the first X-ray tube 1*a*, the second X-ray tube 1*b*, the first X-ray detector 2*a*, the second X-ray detector 2*b* are arranged in either position illustrated in FIG. 3, FIG. 4, FIG. 5 (Step S1.) And, the first template image 105*a* is obtained by clipping the tumor C region from the image 100 including the tumor C (Step S2.) The first template image 105*a* is stored in the template image memory element 65 illustrated in FIG. 6 (Step S3.)

Once the above preparation is completed, the fluoroscopy begins (Step 4) to provide the subject 57 with the therapy. At this time, the X-ray fluoroscopic device of the present invention detects the position of the tumor C so that the position of the radiation to be irradiated relative to the affected area of the subject 57 can be adjusted based on the position of the tumor C.

At this time, the fluoroscopy is conducted at the framing rate around 30 fps relative to the region including the tumor C. Then, referring to FIG. 10, the image including the tumor C is acquired from the images 101 continuously collected every constant time (Step S5.) Thereafter, the template matching element 62 illustrated in FIG. 6 performs the template matching by utilizing the first template image 105*a* stored in advance in the template image memory element 65 relative to the image including the tumor C (Step S6.)

Once the first template matching is completed, the template clipping element 63 illustrated in FIG. 6 clips the image including the tumor C, after the pattern matching identified by the template matching element 62, as the second template image 105*b* (Step S7) and let it store in the template image memory element 65 (Step S8.)

When the therapeutic treatment continues (Step S9), the step turns back to Step S5 and the image including the tumor C is acquired from the next images 102 continuously collected every constant time (Step S5.) Thereafter, the template matching element 62 illustrated in FIG. 6 performs the template matching by utilizing the second template image 105*b* stored just therebefore in the template image memory element 65 relative to the image including the tumor C (Step S6.)

Once the second template matching is completed, the template clipping element 63 illustrated in FIG. 6 clips the image including the tumor C as the next second template image since the pattern matching is identified by the template matching element 62 (Step S7) and let it store in the template image memory element 65 (Step S8.) For the next template matching, the second template image newly stored is utilized.

When the necessary therapeutic operation is completed by repeating these operations (Step S9), the treatment is over.

Thus, according to the X-ray fluoroscopic device of first Embodiment, second Embodiment and third Embodiment, the clipped image this is clipped as the template image including the marker M or the tumor C identified by performing template matching is structurally employed upon template matching thereafter so that even when the non-spherical marker M is employed, when the specific region, tumor C, of the patient is employed, or when the marker M is imaged together with the body structure, the bone region B, the marker M or the tumor C can be suitably recognized so that the position of the marker M or the tumor C can be accurately identified.

REFERENCE OF SIGNS

1*a* First X-ray tube
1*b* Second X-ray tube
2*a* First X-ray detector
2*b* Second X-ray detector
3*a* First pedestal for X-ray tube
3*b* Second pedestal for X-ray tube
4*a* First pedestal for X-ray detector
4*b* Second pedestal for X-ray detector
10 Move passage
11 First rail
12 Second rail
20 Move passage
21 First rail
22 Second rail
53 Gantry
54 Head support element
55 Head
56 Imaging table
57 Subject
61 Control module
62 Template matching element
63 Template clipping element
64 Memory element
65 Template image memory element
66 Display module
85*a* First template image
85*b* Second template image
95*a* First template image
95*b* Second template image
105*a* First template image
105*b* Second template image B Bone region
C Tumor
M Marker*

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An x-ray fluoroscopic device, comprising:
an X-ray tube and an X-ray detector that detects an X-ray that is irradiated from said X-ray tube and passes through a subject,
wherein said X-ray fluoroscopic device specifies the position of a marker or a specific region by collecting images including said marker indwelled inside said subject's body or the specific region of said subject;
said X-ray fluoroscopic device, further comprising:
a template image memory element that stores the image including said marker or said specific region as a template image;
a template matching element that specifies the position of the marker or the specific region relative to the continuously collected images by performing template matching utilizing the template image stored in the template image memory element relative to the continuously collected images, and
a template clipping element that clips the image including said marker or said specific region specified by said template matching element as a template image and lets the template image memory element store said template image; and
wherein said template matching element performs the template matching repeatedly during an X-ray fluoroscopy, in which a present image is compared to said template image that is clipped from the image collected prior to collection of the present image thereof and stored in said template image memory element, relative to the images continuously collected by the X-ray fluoroscopy.

2. The X-ray fluoroscopic device, according to claim 1, wherein:
said template matching element performs said template matching by utilizing the template image that is clipped from the image collected just prior to collection of the image relative to the continuously collected images.

3. The X-ray fluoroscopic device, according to claim 1, wherein:
a plurality of template images clipped from the continuously collected images are stored in said template image memory element, and said template matching element performs the template matching by utilizing a plurality of template images stored in said template image memory element relative to the continuously collected images.

4. The X-ray fluoroscopic device, according to claim 3, wherein:
the template matching element performs said template matching by utilizing the template image clipped from the images collected at a time closer to a collection time of the image among a plurality of template images stored in said template image memory element relative to the continuously collected images.

5. An X-ray fluoroscopic method for specifying the position of a marker and a specific region by detecting an X-ray that is irradiated from an X-ray tube and passes through a subject by an X-ray detector and by collecting images including a marker indwelled inside the subject's body or the specific region of the subject, comprising the steps of:
a step of storing the image including said marker or said specific region as a first template image;
a step of matching the first template that specifies the position of said marker or said specific region relative to the continuously collected images by performing template matching by utilizing said first template image relative to the images continuously collected by an X-ray fluoroscopy;
a step of clipping the template, wherein the images including said marker or said specific region specified are clipped by the step of matching the first template and stored as a second template image; and
a step of matching the second template for specifying the position of said marker or said specific region relative to the continuously collected images by performing template matching utilizing said second template image relative to the images continuously collected by said X-ray fluoroscopy, the step of clipping said template and the step of matching said second template being repeatedly performed multiple times relative to the images continuously collected while performing said X-ray fluoroscopy.

6. The X-ray fluoroscopic method, according to claim 5, wherein:
the template clipping step and the second template matching step are repeatedly performed multiple times relative to the continuously collected images, and
in the second template matching step, the template matching is performed by utilizing the second template image that is clipped from the image collected just prior to collection of the image relative to the continuously collected images.

7. The X-ray fluoroscopic method, according to claim 5, wherein:
the template clipping step and the second template matching step are repeatedly performed multiple times relative to the continuously collected images, and
in the second template matching step, the template matching is performed by utilizing a plurality of second template images relative to the continuously collected images.

8. The X-ray fluoroscopic method, according to claim 7, wherein:
the template matching is performed by utilizing the second template image that is operatively clipped from the images collected at the time closer to the collection time of the image among a plurality of second template images relative to the continuously collected images.

9. An x-ray fluoroscopic device, comprising:
an X-ray tube and an X-ray detector that detects an X-ray that is irradiated from said X-ray tube and passes through a subject,
wherein said X-ray fluoroscopic device specifies the position of a marker or a specific region by collecting images including said marker indwelled inside said subject's body or the specific region of said subject;

said X-ray fluoroscopic device, further comprising:
a template image memory element that stores the image including said marker or said specific region as a template image;
a template matching element that specifies the position of the marker or the specific region relative to the continuously collected images by performing template matching utilizing the template image stored in the template image memory element relative to the continuously collected images, and
a template clipping element that clips the image including said marker or said specific region specified by said template matching element as a template image and lets the template image memory element store said template image;
wherein said template matching element performs the template matching by utilizing the template image that is clipped from the image collected prior to collection of the image continuously collected and stored in said template image memory element, relative to the continuously collected images;
wherein a plurality of template images clipped from the continuously collected images are stored in said template image memory element, and said template matching element performs the template matching by utilizing a plurality of template images stored in said template image memory element relative to the continuously collected images; and
wherein the template matching element performs said template matching by utilizing the template image clipped from the images collected at a time closer to a collection time of the image among a plurality of template images stored in said template image memory element relative to the continuously collected images.

10. An X-ray fluoroscopic method, comprising the steps of:

a step of detecting an X-ray that is irradiated from an X-ray tube and passes through a subject by an X-ray tube;
a step of specifying the position of a marker or a specific region by collecting images including said marker indwelled inside said subject's body or the specific region of said subject;
a template image storing step of storing the image including said marker or said specific region as a first template image;
a first template matching step of specifying the position of said marker or said specific region relative to the continuously collected images by performing template matching utilizing said first template image relative to the continuously collected images;
a template clipping step clipping the image including said marker or said specific region specified by the first template matching step, and storing as a second template image; and
a second template matching step of specifying the position of said marker or said specific region relative to the continuously collected images by performing template matching utilizing said second template image relative to the continuously collected image;
wherein the template clipping step and the second template matching step are repeatedly performed multiple times relative to the continuously collected images;
in the second template matching step, the template matching is performed by utilizing a plurality second template images relative to the continuously collected images; and
wherein the template matching is performed by utilizing the second template image that is operatively clipped from the images collected at the time closer to the collection time of the image among a plurality of second template images relative to the continuously collected images.

* * * * *